United States Patent [19]

Tezel

[11] 4,122,855
[45] Oct. 31, 1978

[54] CUTTING TOOL

[76] Inventor: Jirayr Tezel, 221 Falmouth Rd., Scarsdale, N.Y. 10583

[21] Appl. No.: 212,304

[22] Filed: Dec. 27, 1971

[51] Int. Cl.² .............................................. A61B 17/16
[52] U.S. Cl. ..................................... 128/310; 128/2 B
[58] Field of Search ............... 128/305, 310, 329, 355, 128/2 B

[56] References Cited

U.S. PATENT DOCUMENTS

| 1,123,730 | 1/1915 | Greenfield | 128/310 |
| 2,473,968 | 6/1949 | Paton | 128/305 |
| 3,512,519 | 5/1970 | Hall | 128/305 |
| 3,561,449 | 2/1971 | Bellantoni | 128/305 |

Primary Examiner—John D. Yasko

[57] ABSTRACT

A cutting tool for forming sockets in the skin of the scalp of a person includes a handle having a detachable hollow tubular head open at both ends. The head has a knife edge at one end thereof and is formed with at least one bleed hole extending through a side wall of the head.

13 Claims, 6 Drawing Figures

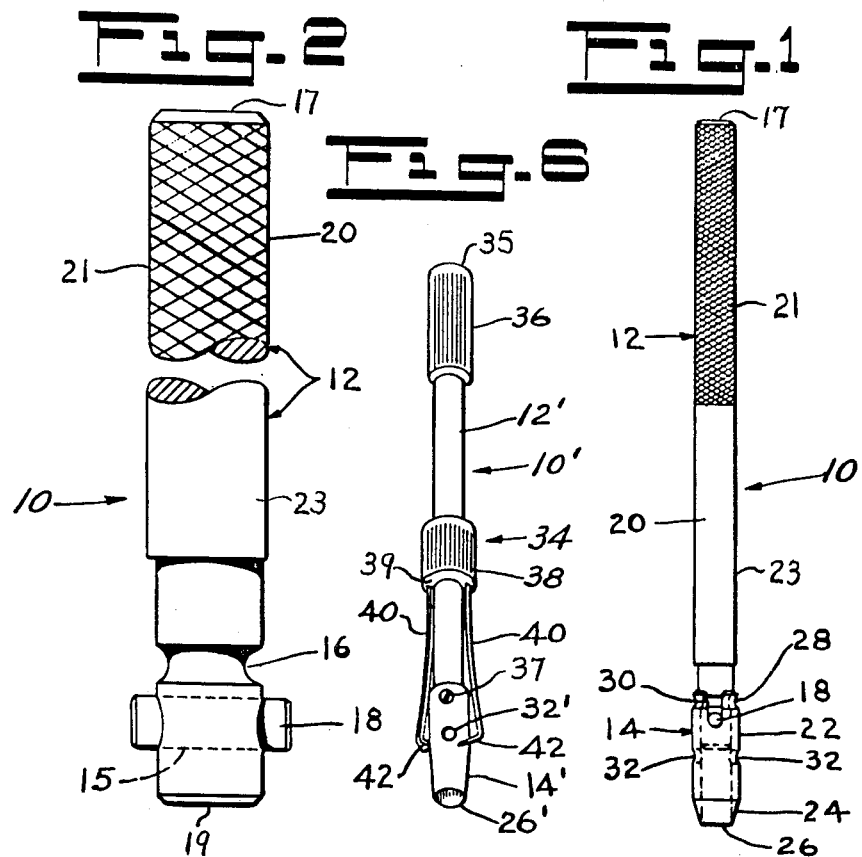
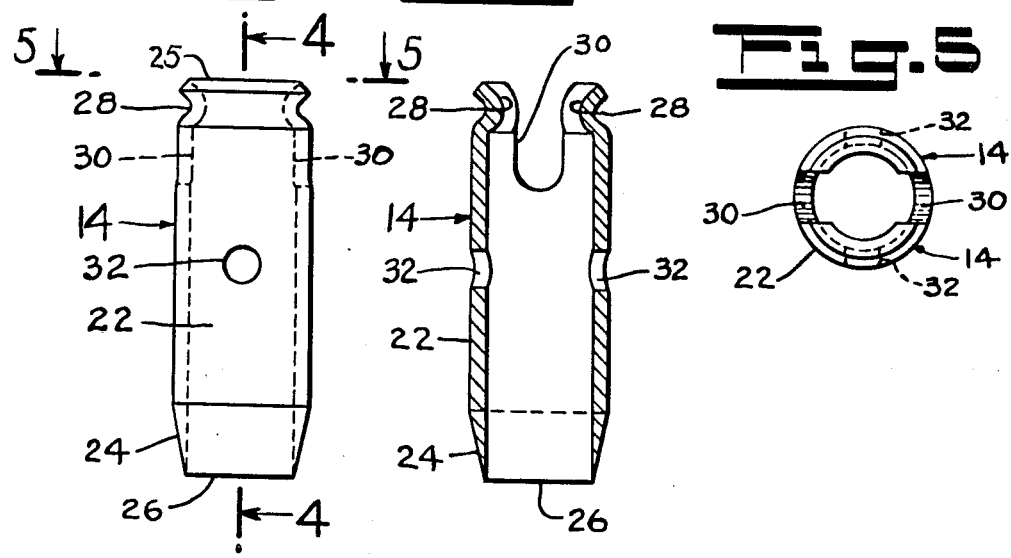

CUTTING TOOL

BACKGROUND OF THE INVENTION

1. Field of the Invention

This invention relates generally to the art of hair transplanting and, in particular, to a cutting tool for boring out plugs of bald scalp skin into which grafts of hair bearing scalp skin may be transplanted.

2. Description of the Prior Art

Cutting tools for boring into or punching out a segment of the anatomy of a human being are known. For instance, U.S. Pat. No. 2,473,968 to Paton discloses a corneal trephine for use in cornea transplanting having a cutting section which includes a razor-sharp edge. Also, Italian Patent No. 280176 to Gomez discloses a tracheotomy device having a knife edge-bearing cutting section. Further, U.S. Pat. No. 2,505,358 to Gusberg discloses a double-cutting biopsy bistoury.

Each of the above tools is useful, however, only for the specific medicinal or surgical purposes for which it was intended. None of them can be practically employed in the art of transplanting hair.

SUMMARY OF THE INVENTION

The present invention relates to a cutting tool specifically designed for boring out plugs of bald scalp skin into which similarly bored out plugs of hair-bearing scalp may be transplanted.

Generally speaking, the present invention relates to a cutting tool of the type above-described comprising a handle having a hollow tubular cutting head detachably affixed to the handle at one end thereof and including a knife edge at the exposed end of the head. The head further includes at least one bleed hole extending through a side wall thereof.

The cutting tool above-described includes two desirable features, each of which contributes to the effectiveness of the tool as a hair transplanting instrument. First, the cutting head is removable which not only facilitates cleaning of the head, but also enables the tool to be used with a variety of heads having different diameter cutting edges.

Second, the cutting head includes a bleed hole which allows blood to be substantially completely drained from about a hair bearing plug of scalp skin as it is cut and removed from the scalp. This enables the hair to be trimmed on the plug without a significant amount of blood congealing thereabout, thus facilitating transplantation of the plug in a bored out hole in a non-hair bearing segment of scalp skin.

In another embodiment of this invention, the tool further includes means for locking a bored-out plug of scalp skin within the cutting head as the tool is removed from the scalp so that the plug may not fall out of the cutting head.

These and other aspects and advantages of the cutting tool of this invention are more clearly described with reference to the accompanying drawing.

BRIEF DESCRIPTION OF THE DRAWING

In the drawing:

FIG. 1 is a side elevation view of one cutting tool of this invention;

FIG. 2 is an enlarged side elevation view of the handle of the cutting tool of FIG. 1;

FIG. 3 is a side elevation view of a detachable cutter head used on the tool of FIG. 1;

FIG. 4 is a cross-sectional view taken along lines 4—4 of FIG. 3;

FIG. 5 is a top plan view of the cutter head of FIG. 3; and

FIG. 6 is a perspective view of another cutting tool of this invention.

DESCRIPTION OF THE ILLUSTRATED EMBODIMENTS

Referring now to FIG. 1 in detail, a cutting tool 10 is shown. Tool 10 is especially designed to implement a hair transplanting procedure requiring segments of bald human scalp to be bored out and replaced with similarly dimensioned hair bearing segments. The tool may, however, be used for other purposes requiring apertures or holes to be formed in a cuttable material. Tool 10 is preferably fabricated of a suitable metal, such as stainless steel, and includes an elongated handle 12 and a removable cutter head 14.

Handle 12 is defined by an elongated body 20 which is preferably circularly cylindrical and is preferably solid. Body 20 includes a corrugated segment 21 extending from one end 17 of the body to a point substantially intermediate end 17 and another end 19 of the body, segment 21 facilitating the handling of the tool. Further, body 20 includes a non-corrugated segment 23 extending from the corrugated segment to body end 19.

Segment 23 includes a transverse hole 15 (FIG. 2) near body end 19 and in which is positioned an elongate pin 18 projecting from opposing sides of body segment 23. An annular groove 16 (FIG. 2) is formed in the body on segment 23 adjacent transverse hole 15 with groove 16 being closer end 17 than hole 15. The purpose of pin 18 and groove 16 is described below.

Referring now specifically to FIGS. 1 and 3–5, cutter head 14 may be seen as including a tubular body 22 which is preferably circularly cylindrical. Body 22 includes a tapered end 24 terminating in a circular knife edge 26 which is desirably about 5/32 inch in diameter.

A pair of opposed bleed holes 32 are formed in the side wall of cutter head body 22 intermediate the ends thereof. Holes 32 permit the drainage of blood from about bored out plugs of scalp and thereby reduce contamination of the hair with such blood. It is not essential for there to be a pair of opposing bleed holes, although such is preferred. For instance, there may be only one bleed hole or there may be more than two.

Body 22 of cutter head 14 further includes a pair of opposed slots 30 formed therein and extending from an end 25 of the cutter head to a point preferably approximately about ¼–⅓ the distance from end 25 to cutting edge 26. Opposing slots 30 each extend transversely a distance substantially equal to the diameter of pin 18 so as to securely receive the extended ends of such pin respectively therein when cutter head 14 is attached to handle body 20 in a manner more fully described below.

Body 22 of cutter head 14 is provided near end 25 with an inwardly directed annular bead 28. The apex of bead 28 lies on a circle having a diameter substantially equal to the inner or apex diameter of groove 16 in handle body 23. The depth of the bead and groove are small and head 22 is sufficiently elastic so that the bead may be snapped into such groove to mount cutting head 14 to tool body 20. It may likewise be snapped out of the groove to detach head 22 from handle body 23.

In assembling the tool 10, cutter head 14 is slid over end 19 of handle 12 and into engagement with body segment 23 thereof. Opposed slots 30 of cutter head 14 are aligned with the projecting ends of the pin 18 as the head is slid onto segment 23 so that the slots respectively receive the projecting ends of the pin to thereby prevent head 14 from turning relative to handle 12. Head 14 is further slid onto handle body segment 23 until annular bead 28 snaps into annular groove 16 in the handle 12 to thereby detachably lock head 14 onto handle 12. Head 14 may be subsequently removed by exerting a sufficient separating force thereon to cause the beaded end 25 of head 14 to expand to cause bead 28 to ride out of groove 16.

In operation, a bald area of the head into which hair is to be grafted, and an area of the head from which hair follicles are to be taken, are both anaesthetized by the injection of a local anaesthetic. Tool 10 is then used to cut out plugs in the bald portion of the scalp thereby leaving sockets. The same punch or cutter 10 is then used to cut out or bore out hair-bearing plugs from the portion of the scalp bearing hair. The hair-bearing plugs are removed from the scalp with blood on the side periphery of the plugs being drained through bleed holes 32. Once each hair-bearing plug is removed, the hair thereon may be trimmed to proper length. The prepared hair-bearing plugs are then placed in the punched-out sockets on the bald scalp where they are held in place by the remaining blood in the sockets which congeals after a short period of time. After bleeding has ceased, the scalp is appropriately dressed and bandaged.

An alternative tool 10' of this invention is shown in FIG. 6. Tool 10' is similar to tool 10 and has an elongated tubular handle 12' and a cutter head 14'. As with tool 10, handle 12' is preferably circularly cylindrical and solid; whereas head 14' is hollow. Tool 10' further includes a plug remover which will be described in detail below.

Desirably, although not necessarily, handle 12' includes an elongated corrugated sleeve 36 at its outer end 35 to facilitate handling of the tool. Of course, handle 12' could be the same as handle 12 or, conversely handle 12 might be constructed like handle 12'. Cutter head 14' is fixed on the other end (not shown) of the handle by means of a screw 37 extending through a threaded transverse hole (not shown) at said other end. Thus, an interlocking bead and accommodating annular groove, such as bead 28 and groove 16 of tool 10, and a transverse pin with accommodating slots, such as pin 18 and slots 30 of tool 10, are not included on tool 10' although such could be employed. Screw 37 and threaded hole in the handle define the means for detachably locking the cutting head to the handle and the means for preventing rotation of the head relative to the handle during assembly.

As with cutter head 14, cutter head 14' is formed with a pair of opposing bleed holes 32' which extend through the side wall of the head at points substantially intermediate the elongate extent of the head. Head 14' further includes a knife edge 26' similar to cutting edge 26 of cutter head 14.

In accordance with an additional feature of this invention, tool 10' includes a plug holder 34 which is constructed from fluted sleeve 38 slidably mounted on handle 12'. Sleeve 38 is preferably only slidable upon the exertion of a small amount of force, such as by the operator of the tool manually pushing the sleeve, although the fit is sufficiently tight that sleeve 38 will remain stationary on handle 12' by friction unless pushed.

Plug holder 34 further includes a pair of opposed spring arms 40 and 40' which are carried on opposing sides of sleeve 38. More specifically, one end of each arm is anchored in an edge 39 of the sleeve. The arms extend longitudinally of the body of the handle and along opposite sides thereof and terminate at outer free ends defined by inwardly turned pointed prongs 42 and 42', respectively.

When sleeve 38 is positioned at a point substantially intermediate the ends of handle 12', prongs 42 and 42' will be in contact with cutter head 14' at a point thereon intermediate the length of the head. When prongs 42 and 42' are in the position shown in FIG. 6, they are pressed against the cutter head by the resiliency of spring arms 40 and 40'. When sleeve 38 is slid down handle 12' toward cutting head 14', the prongs 42 and 42' will correspondingly slide along the outer surface of the head until they pass cutting edge 26' at which point the prongs will snap toward each other as a result of the self bias of the spring arms.

In operation of tool 10', plug holder 34 is normally positioned with sleeve 38 intermediate the ends of handle 12', as shown in FIG. 6. Then a cut is made and sleeve 38 is slid down the handle until prongs 42 and 42' snap into position under the plug whereupon outward movement of the tool removes the plug. The prongs, of course, prevent the plug from falling out of the head as the tool is lifted from the scalp. It can thus be said, therefore, that plug holder 34 releasably locks a cut plug of skin within the head.

While the invention has been described primarily for use in connection with hair transplants, it will be recognized that the device has far broader applications than that. Thus, for example, the device may be used for any of the known purposes of a skin punch such as, for example, the taking of biopsies.

In this connection, the modification of the invention shown in FIG. 6 is especially desirable for use in the taking of a biopsy of fragile diseased skin in that the holding means will function to preserve the specimen without any likelihood of damage as can result from the handling of such diseased fragile skin by forceps or the like.

Although the invention has been described with reference to a number of illustrated embodiments, the scope of the invention is not to be so limited. Rather, the invention is deemed to include obvious modifications and alterations to the embodiments above described. The precise scope of this invention is to be defined by the following claims.

What is claimed is:

1. A cutting tool for forming removable plugs and sockets in the skin of the scalp of a person, comprising:
    (a) an elongated handle;
    (b) a hollow cylindrical cutting head detachably mounted to the handle at one end thereof;
    (c) the head having a tapered portion at one end thereof terminating in a circular knife edge for cutting into said skin; and
    (d) the head including at least one bleed hole extending through the side wall thereof.

2. The tool of claim 1, wherein the head includes a pair of opposed bleed holes extending through the side wall thereof.

3. The tool of claim 1, further including means for preventing the head from turning relative to the handle when mounted thereon.

4. The tool of claim 1, further including means for detachably mounting the head to the handle.

5. The tool of claim 3, wherein the preventing means comprises:
   (a) a transverse hole defined in the handle and a pin disposed in the hole and having its ends projecting outwardly of the handle on opposite sides thereof; and
   (b) the cutter head has a pair of opposed slots extending from the other end thereof and receiving therein the projecting ends of the pin.

6. The tool of claim 4, wherein the handle is a solid cylinder and the means for detachably mounting the head to the handle comprises
   (a) an annular groove defined in the handle adjacent said one end thereof; and
   (b) an annular bead formed on the interior of the head adjacent its other end, the bead being snap fittable into the annular groove of the handle upon the head being slid onto the handle.

7. The tool of claim 5, wherein:
   (a) the handle is a solid cylinder, and the head being detachably mounted on said handle by an annular groove defined in the handle adjacent said one end thereof; and
   (b) an annular bead formed on the interior of the head adjacent its other end, the bead being snap fittable into the annular groove of the handle upon the head being slid onto the handle for detachably mounting the head onto the handle.

8. The tool of claim 7, wherein the head includes a pair of opposed bleed holes extending through the side wall thereof.

9. The tool of claim 1, further comprising means for releasably holding a plug of scalp skin within the head.

10. The tool of claim 9, wherein the releasable holding means comprises:
    (a) a sleeve slidably mounted on the handle;
    (b) a pair of opposed elongated spring arms carried by the sleeve and extending along the body of the handle; and
    (c) a pair of opposed inwardly extending prongs, one on each of the pair of spring arms, the prongs being biased by the spring arms to snap under the knife edge of said hub for holding a plug of skin disposed therewithin.

11. A cutter tool for forming removable plugs and sockets in the skin of the scalp of a person, said tool comprising an elongated solid cylindrical handle, a tubular cutting head on one end of the handle and means for securing the head on the handle, said cutter head having a tapered portion at one end thereof terminating in a circular knife edge, said means for securing the head on the handle including an annular groove in the body of the handle adjacent one end thereof and an annular bead on the interior of the tubular cutting head adjacent its inner end and adapted to snap into the groove upon assembly.

12. A cutter tool for forming removable plugs and sockets in the skin of the scalp of a person as defined in claim 11, a transverse pin fixed on the handle below the annular groove thereof and with its ends projecting outwardly from the opposite sides thereof, said cutter head having opposed slots intersecting one end and the annular bead thereof adapted to coact with the projecting ends of the pin for assembling the cutter head on the handle and for preventing the cutter head from turning thereon.

13. A cutter tool for forming removable plugs and sockets in the skin of the scalp of a person, said tool comprising an elongated solid cylindrical handle, a tubular cutting head on one end of the handle and means for securing the head on the handle, said cutter head having a tapered portion at one end thereof terminating in a circular knife edge, and a device for removing a plug of skin cut from the scalp, said device including a sleeve slidably mounted on the handle, and opposed elongated spring arms carried by the sleeve extending along the body of the handle, and opposed inwardly extending prongs on the free ends of the arms adapted to snap into the under surface of the cut plug in the scalp whereby longitudinal movement of the cutter tool removes the cut plug from the scalp.

* * * * *